(12) United States Patent
Gershon et al.

(10) Patent No.: US 9,937,112 B2
(45) Date of Patent: Apr. 10, 2018

(54) DOPING OF ZINC OXIDE PARTICLES FOR SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/082,687

(22) Filed: Mar. 28, 2016

(65) Prior Publication Data

US 2017/0065506 A1    Mar. 9, 2017

Related U.S. Application Data

(60) Provisional application No. 62/213,658, filed on Sep. 3, 2015.

(51) Int. Cl.
| | | |
|---|---|---|
| *A61K 8/27* | (2006.01) | |
| *A61K 8/11* | (2006.01) | |
| *A61Q 17/04* | (2006.01) | |
| *A61K 8/19* | (2006.01) | |
| *A61K 8/02* | (2006.01) | |

(52) U.S. Cl.
CPC ........... *A61K 8/27* (2013.01); *A61K 8/0241* (2013.01); *A61K 8/19* (2013.01); *A61Q 17/04* (2013.01); *A61K 2800/262* (2013.01); *A61K 2800/42* (2013.01); *A61K 2800/651* (2013.01)

(58) Field of Classification Search
CPC ...... A61K 8/27; A61K 8/19; A61K 2800/262; A61Q 17/04

See application file for complete search history.

(56) References Cited

U.S. PATENT DOCUMENTS

| | | | |
|---|---|---|---|
| 3,761,261 A | 9/1973 | Ono et al. | |
| 3,863,007 A | 1/1975 | Warner, Jr. | |
| 4,549,195 A | 10/1985 | Bluzer | |
| 5,011,782 A | 4/1991 | Lamb | |
| 5,147,125 A | 9/1992 | Austin | |
| 5,223,250 A | 6/1993 | Mitchell | |
| 5,441,726 A * | 8/1995 | Mitchnick | A61K 8/27 106/14.34 |
| 5,534,056 A | 7/1996 | Kuehnle | |
| 6,419,909 B1 | 7/2002 | Lorant | |
| 7,241,399 B2 | 7/2007 | Haubold | |
| 9,056,063 B2 | 6/2015 | Hanson | |
| 9,144,535 B1 | 9/2015 | Daly et al. | |
| 9,144,536 B1 | 9/2015 | Daly et al. | |
| 2002/0122832 A1 | 9/2002 | Hanke | |
| 2003/0102099 A1 | 6/2003 | Yadav | |
| 2004/0209081 A1 | 10/2004 | Hagihara | |
| 2005/0008861 A1 | 1/2005 | Yadav et al. | |
| 2005/0048010 A1* | 3/2005 | Kliss | A61K 8/044 424/59 |
| 2005/0208005 A1 | 9/2005 | Giroud | |
| 2005/0227063 A1 | 10/2005 | Lawandy | |
| 2005/0265935 A1 | 12/2005 | Hollingsworth | |
| 2006/0228310 A1 | 10/2006 | Lyth | |
| 2006/0270053 A1 | 11/2006 | Tilak | |
| 2007/0280895 A1 | 12/2007 | Weimer | |
| 2008/0220026 A1 | 9/2008 | Maltra | |
| 2009/0022765 A1 | 1/2009 | Chung et al. | |
| 2009/0104130 A1 | 4/2009 | Bernstein | |

(Continued)

FOREIGN PATENT DOCUMENTS

| | | |
|---|---|---|
| CN | 103071535 A | 5/2013 |
| EP | 1889810 A1 | 2/2008 |

(Continued)

OTHER PUBLICATIONS

Definitions of "incorporate" from Merriam-Webster, Vocabulary. com. Downloaded from https://www.merriam-webster.com/dictionary/incorporate and https://www.vocabulary.com/dictionary/incorporate respectively May 11, 2017.*
Synonyms of "incorporate" downloaded from http://www.thesaurus.com/browse/incorporate on May 11, 2017.*
Author: Tariq Jan, et al.; title: Sn doping induced enhancement in the activity of ZnO nanostructures against antibiotic resistant S. aureus bacteria; Int J Nanomedicine. vol. 8, pp. 3679-3687; Published online Sep. 30, 2013.*
Author: Bhatti, et al.; title: Optical Properties of Chromium & Cobalt Doped Zinc Oxide Powder Prepared by Sol-Gel Combustion Method, With the Assistance of Microwave Radiations; International Journal of advanced Tech. in Engineering and science; vol. 3, issue 10; pp. 80-85; published Oct. 2015.*
Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.

(Continued)

*Primary Examiner* — Yanzhi Zhang
(74) *Attorney, Agent, or Firm* — Ryan, Mason & Lewis, LLP

(57) ABSTRACT

Zinc oxide compositions as well as techniques for doping ZnO particles for sunscreen applications are provided herein. A method includes selecting one or more dopants to be incorporated into one or more zinc oxide particles in a sunscreen composition, wherein the one or more dopants comprise chromium, cobalt, gallium, and/or tin, and wherein said selecting is based on one or more optical properties associated with each of the dopants, and incorporating the selected dopants into the zinc oxide particles to create the sunscreen composition. A composition includes multiple zinc oxide particles suspended within a medium forming sunscreen composition, and one or more dopants incorporated into each of the multiple zinc oxide particles, wherein the one or more dopants comprise chromium, cobalt, gallium, and/or tin, and wherein each of the dopants imparts one or more optical properties to the zinc oxide particle within which the dopant is incorporated.

5 Claims, 1 Drawing Sheet

(56) References Cited

U.S. PATENT DOCUMENTS

| | | | |
|---|---|---|---|
| 2009/0258072 | A1 | 10/2009 | Schlossman |
| 2009/0258230 | A1 | 10/2009 | Schlossman |
| 2010/0008872 | A1 | 1/2010 | Katusic |
| 2010/0055138 | A1 | 3/2010 | Margulies |
| 2011/0268678 | A1 | 11/2011 | Armstrong |
| 2013/0216834 | A1 | 8/2013 | Hashimoto |
| 2014/0142213 | A1 | 5/2014 | Weiss |
| 2015/0283059 | A1 | 10/2015 | Nagare |
| 2016/0082513 | A1 | 3/2016 | Niedermeyer |

FOREIGN PATENT DOCUMENTS

| | | |
|---|---|---|
| JP | 09059591 A | 3/1997 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2012046204 A1 | 4/2012 |
| WO | 2013040149 | 3/2013 |
| WO | 2014049139 A1 | 4/2014 |
| WO | 2014077189 | 5/2014 |
| WO | 2016020168 A1 | 2/2016 |

OTHER PUBLICATIONS

Sardar et al., Optical-absorption intensities and intermanifold emission cross sections of trivalent erbium ions in calcium fluorophosphate, Journal of Applied Physics, Sep. 2005.

Lu et al., 2008—White Up-Conversion Luminescence in Rare-Earth-Ion-Doped YAlO3 Nanocrystals, J. Phys. Chem. C 2008, 112, 15071-15074.

Refractive index of ZnO (Zinc oxide)—Bond-o, http://refractiveindex.info/?shelf=main&book=ZnO&page=Bond-o, Mar. 25, 2016.

Refractive index of SiO2 (Silicon dioxide, Silica, Quartz)—Malitson, http://refractiveindex.info/?shelf=main&book=SiO2&page=Malitson, Mar. 25, 2016.

Schubert et al., Design of multilayer antireflection coatings made from co-sputtered and low-refractive-index materials by genetic algorithm. Optics Express vol. 16, No. 8, 2008.

Law et al., ZnO—Al2O3 and ZnO—TiO2 Core-Shell Nanowire Dye-Sensitized Solar Cells. J. Phys. Chem. B 2006, 110, 22652-22663.

Pu et al., Core/shell structured ZnO/SiO2 nanoparticles: Preparation, characterization and photocatalytic property. Applied Surface Science 257 (2010) 393-397.

Mantz et al., Progress in Organic Coatings 47 (2003) 432-442, "A multiple-scattering model analysis of zinc oxide pigment for spacecraft thermal control coatings."

Song et al., Toxicology Letters 199 (2010) 389-397, "Role of the dissolved zinc io and reactive oxygen species in cytotoxicity of ZnO nanoparticles."

Bohren et al., "Absorption and Scattering of Light by Small Particles", Wiley-VCH, © 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation."

NanoComposix, Silver Nanoparticles: Optical Properties, http://nanocomposix.com/pages/silver-nanoparticles-optical-properties, Apr. 20, 2016.

Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011—Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152.

Luo et al., Facile synthesis of composition-tuned ZnO/ZnxCd1-xSe nanowires for photovoltaic applications, Nanoscale Research Letters (2015) 10:181.

List of IBM Patents or Applications Treated as Related.

Naylor et al. "Sunscreens," accessed 2017, http://telemedicine.org/sundam/sundam2.4.2.html.

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.

Ultraviolet Radiation and the INTERSUN Programme [online]. WHO, Nov. 2003 [retrieved on Jun. 8, 2017]. Retrieved from the internet <http://www.who.int/uv/uv_and_health/en/>.

Cuprous Oxide, Chemical Book, pp. 1-4, Accessed Sep. 18, 2017, https://www.chemicalbook.com/ProductChemicalPropertiesCB9853041_EN.htm.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, pp. 1-4.

* cited by examiner

DOPING OF ZINC OXIDE PARTICLES FOR SUNSCREEN APPLICATIONS

CROSS-REFERENCE TO RELATED APPLICATIONS

The present application claims priority to U.S. Provisional Application Ser. No. 62/213,658, filed Sep. 3, 2015, incorporated by reference herein.

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions, methods of fabrications thereof and methods of use thereof are provided. An exemplary method can include steps of selecting one or more dopants to be incorporated into one or more zinc oxide particles in a sunscreen composition, wherein the one or more dopants comprise at least one of chromium, cobalt, gallium, and tin, and wherein said selecting is based on one or more optical properties associated with each of the dopants. The method also includes incorporating the one or more selected dopants into the one or more zinc oxide particles to create the sunscreen composition.

In another embodiment of the invention, a composition can include multiple zinc oxide particles suspended within a medium forming sunscreen composition, and one or more dopants incorporated into each of the multiple zinc oxide particles, wherein the one or more dopants comprise at least one of chromium, cobalt, gallium, and tin, and wherein each of the dopants imparts one or more optical properties to the zinc oxide particle within which the dopant is incorporated.

These and other objects, features and advantages of the present invention will become apparent from the following detailed description of illustrative embodiments thereof, which is to be read in connection with the accompanying drawings.

DETAILED DESCRIPTION

Figure 1:
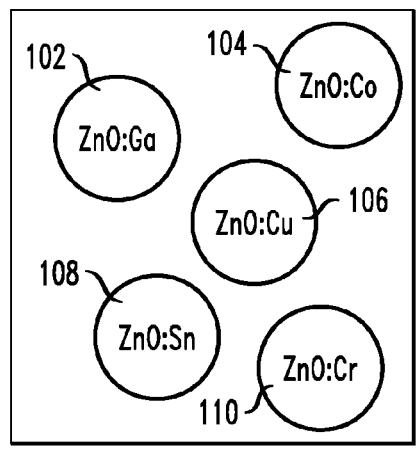
FIG. 1 is a diagram illustrating doped ZnO particles, according to an exemplary embodiment of the invention.

As described herein, an embodiment of the present invention includes ZnO compositions as well as techniques for doping ZnO particles for sunscreen applications. As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm). As used herein, "scattering" refers to the deflection of rays of visible light from the rays' original path due to interaction with particle surfaces.

As further detailed herein, one or more embodiments of the invention include generating ZnO compositions and methods of use thereof for effectively modifying the band gap of a ZnO composition via the incorporation of one or more additional materials into the composition. For example, at least one embodiment of the invention can include modifying the absorption onset of a ZnO composition from approximately 375 nm to approximately 410 nm.

At least one embodiment of the invention includes doping ZnO particles with one or more transition metals to increase absorption by the ZnO particles in sunscreen applications. By way of example, in one or more embodiments of the invention, the addition of one or more dopants to ZnO particles can result in 400 nm absorption. Such addition can encompass up to approximately 10% (atomic percent) of dopant. Example dopants, in accordance with one or more embodiments of the invention, can include chromium (Cr), copper (Cu), cobalt (Co), gallium (Ga), aluminum (Al), and/or tin (Sn).

In at least one embodiment of the invention, addition of one or more dopants to ZnO particles can decrease the band gap of the ZnO particles.

As used herein, and as is to be appreciated by one skilled in the art, a band gap represents the minimum amount of energy required to cause electrons to transition from the collection of electronic ground states (that is, the valence band) to an available unfilled excited electronic state (that is, the conduction band). By way merely of illustration, in a perfect semiconductor, there are no available electronic states in between the valence band and the conduction band. However, in imperfect materials, various defects can introduce electronic states into this otherwise forbidden energy gap. For example, in at least one embodiment of the invention, addition of one or more dopants to ZnO particles can improve the absorption properties of the ZnO particles in a spectral region of interest (for instance, 280-410 nm).

There are multiple mechanisms by which dopants can increase absorption in ZnO in the spectral range of 280-410 nm. Such mechanisms can include, for example: (i) the introduction of electronic states (associated with the dopants) inside of the band gap of ZnO, where these states may be optically active (that is, electrons can be promoted to or from these states into and/or out of the conduction and valence bands); (ii) dopants can cause lattice strain due to a difference in size between the host atoms and the impurity atoms (dopants), and this strain can increase or decrease the band gap of ZnO depending on whether the strain is compressive or tensile; and (iii) the presence of dopants and/or defects can induce band tailing in the ZnO due to local electronic or structural fluctuations, which can increase sub-band gap absorption.

Additionally, in one or more embodiments of the invention, addition of one or more dopants to ZnO particles can introduce one or more additional states inside of the band gap of the ZnO particles, which allow and/or facilitate the ZnO particles to absorb lower-energy light. Due to differences in local bonding between the impurity atom (dopant) and the host crystal (ZnO, for example), new electronic states can be introduced inside of the band gap (of the host crystal). Additionally, if there is more than one configuration for the dopant to incorporate into the structure, the same dopant can introduce multiple states. For example, if an impurity atom can occupy either a Zn site or an interstitial site, then it is possible for that impurity atom to introduce more than one type of electronic state into the band gap of ZnO.

FIG. 1 is a diagram illustrating doped ZnO particles, according to an embodiment of the invention. By way of illustration, FIG. 1 depicts multiple ZnO particles doped with various dopants within a sunscreen composition. Specifically, FIG. 1 depicts a Ga-doped ZnO particle 102, a Co-doped ZnO particle 104, a Cu-doped ZnO particle 106, a Sn-doped ZnO particle 108, and a Cr-doped ZnO particle 110. Accordingly, as illustrated in FIG. 1, a collection of multiple ZnO particles within a sunscreen composition can be doped by multiple distinct dopants. Alternatively, in one or more embodiments of the invention, a collection of multiple ZnO particles within a sunscreen composition can be doped by a single type of dopant. Further, multiple dopants can be used in connection with a single ZnO particle.

Figure 2:
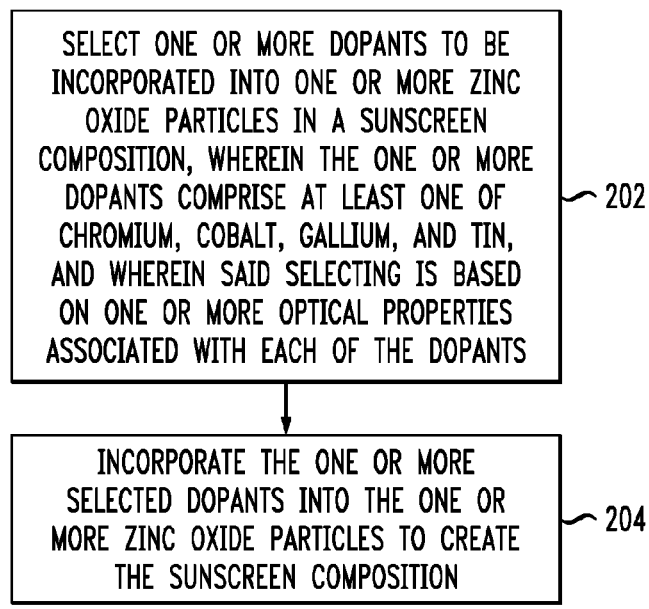
FIG. 2 is a flow diagram illustrating techniques, according to an embodiment of the invention.

FIG. 2 is a flow diagram illustrating techniques, according to an embodiment of the present invention. Step 202 includes selecting one or more dopants to be incorporated into one or more zinc oxide particles in a sunscreen composition, wherein the one or more dopants comprise at least one of chromium, cobalt, gallium, and tin, and wherein said selecting is based on one or more optical properties associated with each of the dopants.

The optical properties can include, for example, increasing the light absorption capabilities of the one or more zinc oxide particles. In such an embodiment of the invention, the increased absorption of light can include 400 nanometer absorption capabilities. Additionally, the optical properties can include decreasing the band gap of the zinc oxide particles, providing a color center within the zinc oxide particles, and/or introducing one or more additional states inside the band gap of the zinc oxide particles.

In one or more embodiments of the invention, the one or more dopants can include two or more dopants to be incorporated into the one or more zinc oxide particles. Additionally, in one or more embodiments of the invention, the one or more dopants can include a combination of two or more dopants to be incorporated into each of the one or more zinc oxide particles. Further, in at least one embodiment of the invention, the one or more dopants can include a single dopant to be incorporated into the one or more zinc oxide particles.

Step 204 includes incorporating the one or more selected dopants into the one or more zinc oxide particles to create the sunscreen composition. Incorporating can include incorporating up to approximately ten atomic percent, of the sunscreen composition, of the one or more selected dopants into the one or more zinc oxide particles.

Also, an additional embodiment of the invention includes a composition that includes multiple zinc oxide particles suspended within a medium forming sunscreen composition, and one or more dopants incorporated into each of the multiple zinc oxide particles, wherein the one or more dopants comprise at least one of chromium, cobalt, gallium, and tin, and wherein each of the dopants imparts one or more optical properties to the zinc oxide particle within which the dopant is incorporated. In such a composition, the one or more dopants incorporated into each of the multiple zinc oxide particles can include up to approximately ten atomic percent, of the sunscreen composition, of the one or more dopants.

Also, in such a composition, the optical properties can include at least one of: (i) increasing the light absorption capabilities of the zinc oxide particle within which the dopant is incorporated, (ii) decreasing the band gap of the zinc oxide particle within which the dopant is incorporated, (iii) providing a color center within the zinc oxide particle within which the dopant is incorporated, and (iv) introducing one or more additional states inside the band gap of the zinc oxide particle within which the dopant is incorporated. Such optical properties achieve the objective of increasing ZnO absorption in the spectral region of 280-400 nm.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, effectively modifying the band gap of a ZnO composition via the incorporation of one or more dopants into the composition.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A composition comprising:
multiple zinc oxide particles suspended within a medium forming a sunscreen composition; and
multiple dopants incorporated into the multiple zinc oxide particles, wherein the dopants consist of copper, chromium, cobalt, gallium, aluminum, and tin, and wherein each of the dopants imparts one or more optical properties to the zinc oxide particle within which the dopant is incorporated.

2. The composition of claim 1, wherein the dopants incorporated into the multiple zinc oxide particles comprise up to approximately ten atomic percent, of the sunscreen composition, of the dopants.

3. The composition of claim 1, wherein the one or more optical properties comprise increasing the light absorption capabilities of the zinc oxide particle within which the dopant is incorporated.

4. The composition of claim 3, wherein the increased absorption of light comprises 400 nanometer absorption capabilities.

5. The composition of claim 1, wherein the one or more optical properties comprise introducing one or more additional states inside the band gap of the zinc oxide particle within which the dopant is incorporated.

* * * * *

UNITED STATES PATENT AND TRADEMARK OFFICE
CERTIFICATE OF CORRECTION

PATENT NO. : 9,937,112 B2
APPLICATION NO. : 15/082687
DATED : April 10, 2018
INVENTOR(S) : Talia S. Gershon et al.

Page 1 of 1

It is certified that error appears in the above-identified patent and that said Letters Patent is hereby corrected as shown below:

In the Claims

Column 5 Line 10-14 in Claim 2, please remove ", of the dopants"

Signed and Sealed this
Eleventh Day of December, 2018

Andrei Iancu
*Director of the United States Patent and Trademark Office*